United States Patent [19]

Baldini et al.

[11] Patent Number: 4,685,917

[45] Date of Patent: Aug. 11, 1987

[54] STERILIZABLE VALVULAR SYSTEMS FOR FLEXIBLE CONTAINERS

[75] Inventors: Luciano Baldini, Tirano, Italy; Alberto Siccardi, Lugano, Switzerland

[73] Assignee: Bieffe S.p.A., Italy

[21] Appl. No.: 669,008

[22] Filed: Nov. 7, 1984

[30] Foreign Application Priority Data

Nov. 14, 1983 [IT] Italy .............................. 23693 A/83

[51] Int. Cl.[4] ...................... A61B 19/00; A61M 37/00

[52] U.S. Cl. .................................... 604/411; 604/415; 604/408; 604/88

[58] Field of Search ................... 604/88, 87, 408, 411, 604/414, 415, 905

[56] References Cited

U.S. PATENT DOCUMENTS

| | | | |
|---|---|---|---|
| 2,704,075 | 3/1955 | Cherkin | 604/408 |
| 3,390,677 | 7/1968 | Razimbaud | 604/414 |
| 4,326,574 | 4/1982 | Pallaroni et al. | 604/415 |
| 4,364,387 | 12/1982 | Larkin | 604/411 |
| 4,547,900 | 10/1985 | Larkin et al. | 604/408 |

*Primary Examiner*—Richard C. Pinkham
*Assistant Examiner*—Benjamin Layno
*Attorney, Agent, or Firm*—Ostrolenk, Faber, Gerb & Soffen

[57] ABSTRACT

A valvular system for the extraction and/or addition of liquids held in flexible sterilizable containers of plastic material, including an elastomeric semirigid hydraulic seal having two major superior and inferior faces and at least one minor lateral face. A housing of plastic material for the said elastomeric element. The valvular system is characterized in that at least one of the said major faces of the elastomeric element is at least partially spaced from the housing body.

7 Claims, 10 Drawing Figures

FIG. 1
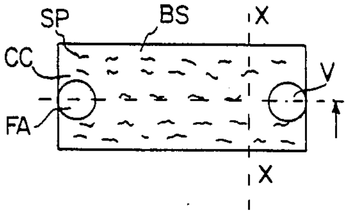
FIG. 2
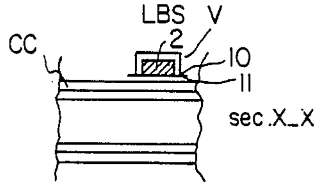
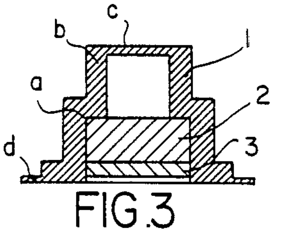
FIG.3
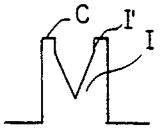
FIG.6
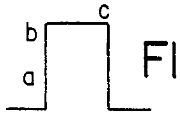
FIG.4
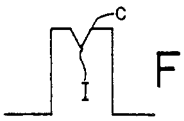
FIG.5
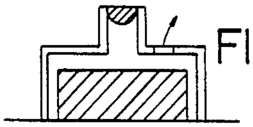
FIG.9
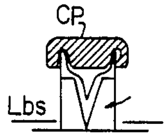
FIG.8
FIG.13
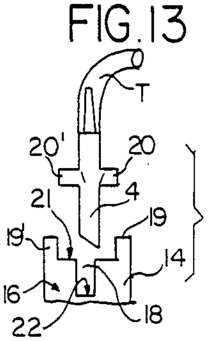
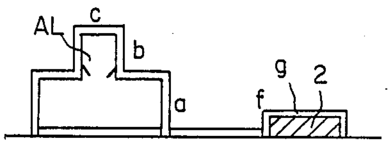
FIG. 7
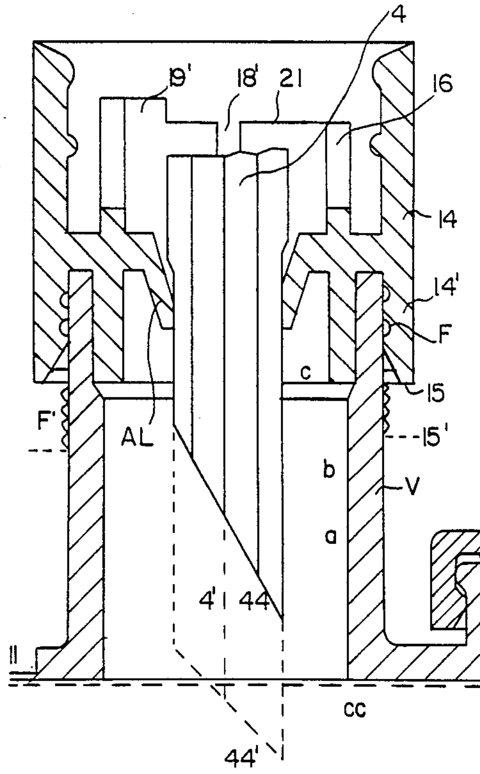
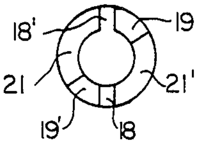
FIG. 14
FIG.11
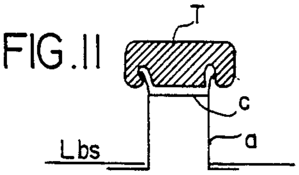
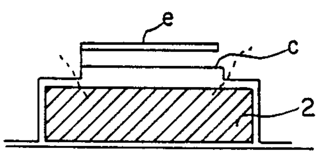
FIG.10
FIG. 12

STERILIZABLE VALVULAR SYSTEMS FOR FLEXIBLE CONTAINERS

1. FIELD OF THE INVENTION

The present invention relates to a valvular system for the extraction and/or addition of liquids held in flexible sterilizable bags of plastic material, including an elastomeric semirigid hydraulic seal having two major superior and inferior faces and at least one minor lateral face, and a housing of plastic material. In particular the invention relates to valvular systems of substantially plastic material, sterilizable at 121.5° C. or higher temperatures, which is suitable for assuring the extraction and-/or the addition of substantially liquid substances from-/into flexible containers. The flexible containers comprise a body of rigid or semirigid plastic material, that can be penetrated by sharpened members for the extration and/or addition of the liquids. The valvular system is applied directly on the wall or in the inner face of the same wall of the flexible container e.g. by welding, glueing and/or seaming, and is provided with one or more pieces of semirigid material with elastic memory, prevalently rubber, with one or more pieces for the guide, the support, the locking and the seal of the sharpened members extracting the liquid and with one or more covers and/or membranes and/or prevalently plastic film, suitable for keeping a sterile room in the inside of the valvular system, the said sterility being eventually produced after the application of the system to the flexible container.

2. STATEMENT OF THE PRIOR ART

Valvular systems for flexible containers are described in the following cited references.

In particular the U.S. Pat. No. 2,704,075 describes flexible containers provided with an elastic element (e.g. of rubber or resilient plastic material) eventually formed as a continuous rim on the container when it is extruded, e.g. after having trapped it into a plastic envelope of PVC or polyethylene that shows edges protruding beyond the perimeter of the elastic element. Generally the valvular element is fastened to the container or is kept sterile by a "Scotch Tape" band that is removed at the moment of the use. The containers and the valve according to the present Patent have not had commercial or experimental application (traceable).

The U.S. Pat. No. 4,326,574 of the Assignee describes a valve type made-up of an elastic material disc (e.g. rubber) contained in an envelope made-up of a two-layer film portion and of a portion of triple laminates, that are glued to the elastomeric element and forms a crown welded and/or glued to the walls of the flexible container. The practical fulfilment of this system has shown some drawbacks e.g. as the perforation could not be made by means of a great sort of perforators available on the market and this valve did not allow the total liquid outlet from the flexible container; further it requires a notable effort for the perforation, comprising the integrity of the same container.

SUMMARY OF THE INVENTION

The first object of the present invention is now to provide a valvular system that eliminates the above mentioned drawbacks, that is easy to apply on the wall of a flexible container, that can be sterilized at temperature of at least 121.5° C. and allows the complete emptying of the flexible container.

Another object of the present invention is to provide a valvular system that can be easily perforated by any sharpened member type, normally used for the extraction of liquids held in flexible containers. A sterile chamber in the valvular system prevents the contamination of the liquid and further allows a seal and a sure locking of the said perforating body in order to prevent leakage and the disjunction of the defluxion device during the use owing to the effect of its gravity force.

Another object of the invention is to provide a valvular two-way system: i.e. one main way with or without elastomeric elements that allows the main use, that is the extraction of the liquid held in the container and a secondary way provided with elastic memory elements that allows possible addition and/or extraction to/from the container by needles or syringes and realizes the hermetic closing when the operation is over.

A further object the present invention is to provide a valvular system having one, two or more ways of the previously described type and further provided permanently, on at least one of the said main ways, with an embodied defluxion device so that it is assured a closed and sterile connection, already at the moment of the preparation, between the container and the patient body.

These and other objects are obtained by a valvular system that is now characterized in that at least one of the said major faces of the elastomeric element is at least partially remotely spaced from the housing body. Preferably the housing body shows a protuberance in correspondance of the major face with a remotely spaced part. The housing body has a zone having substantially the dimensions of the elastomeric element and a step zone overlaying the major face of the said element. The wall part of the housing body remotely spaced from the corresponding major face of the elastomeric element shows an indentation preferably having an upset cone form, for making easier the penetration of sharpened members producing the extration or the addition of the liquid into and respectively from the bag.

BRIEF SUMMARY OF THE DRAWINGS

The various features and advantages of the invention will appear more clearly in the following description of some preferred but not limited forms, represented in the annexed drawings, in which the FIGS. 1 and 2 are respectively a schematic section view of a bag supplied with conventional valve and the FIGS. from 3 to 12 are schematic and partial section views of the valvular system according to the invention. FIG. 13 is a schematic fragmentary view of the defluxor of FIG. 12. FIG. 14 is a schematic top view of the defluxor of FIG. 13.

DESCRIPTION OF THE PREFERRED EMBODIMENTS

To briefly illustrate the ideas, the FIG. 1 shows schematically a flexible container BS (e.g. a bag filled with perfusional solution SP) comprising an holding body CC supplied with a suspension means (e.g. a hole FA) at one end and, e.g. with a valvular system V at the opposite end.

The FIG. 2 (section of the FIG. 1 with a longitudinal plane having the trace represented by the dashed line X—X) shows with sole illustrative aims that the body CC is made by a multilayer composite film e.g. a triple laminate $L_{BS}$ and that the valve V is supplied with a plastic element 2 e.g. between flexible walls 10 and 11 that allow its welding to the body CC (see U.S. Pat. No 4,326,574).

As the figures show, the valvular system according to the invention (FIG. 3) is now made-up by a body 1 of prevalently plastic material (preferably of homo-co-tri-polymer of olefines, styrene, diene, etc.) provided with a main part (a) on which it is blended a protruding zone (b) which guarantees the penetration of the defluxion device (not represented in FIG. 3, but partially visible in FIG. 12) for an intermediate depth e.g. of 16–18 mm. (for allowing the emptying of the container when V is on the bottom of BS) and with a closing wall, (c) (e.g. membrane) that contains the valvular room towards the outside. In some cases the above mentioned body (a) can be supplied with a inferior crown (d) having a proper thickness (e.g. from 0.1 to 0.6 mm.) suitable for being welded to the flexible container BS. The valvular system according to the FIG. 3 is generally completed with an element having elastic memory prevalently of rubber 2 for realizing the hydraulic radial and axial seal to the same body (a) of the valve and with a closing element 3 of prevalently plastic material, preferably made with the same material of the valve body (a) and assembled under pressure in the lower part of (a) underlying the bottom of the elastic element 3.

According to the FIG. 4, the protruding zone (b) of the valve body 1 can be the direct extension of the zone (a) so that this total height of the valvular assembly is respected, for making it suitable for the most part of defluxion devices present on the market.

In some cases the hydraulic seal in axial and/or radial direction can be improved by the presence of some continuous protuberances on the relevant contact surfaces between the body 1 and the elastic element 2, and/or between the said elastic element 2 and the closing element 3; these protuberances can have a circular, triangular, square, rectangular, elliptic section or any possible combination of the listed curves and can be obtained during the fabrication of the said element on one or more of them. Preferably the protuberances realized on an element are in correspondance with recesses in the other element; being these protuberances and recesses intuitive, they were not represented for not complicating the drawings. The valvular system according to the invention can be realized in some cases only from the body 1 and from the elastic element 2, the closing of the inner chamber being obtained with the inner wall $L_{BS}$ of the container BS on which the valvular system V is applied.

According to another feature of the invention, the closing wall (c) of the valvular body 1 shows an indentation zone having section (cylindrical, conical, elliptical, spheric, plane, ecc. shape) suitable for helping the penetration of the defluxion device into the same body (c). Preferably the indentation I has an inverted cone shape (FIG. 5) possibly preceded by a cylindrical portion I' as the FIG. 6 shows.

A further embodiment of the present invention, according to the FIGS. 11 and 8 is represented by a valve in which the membrane (c) is foreseen in the inside of the body (a) (and not in the outside as in the former figures) and it can constitute a seat for a little tap T (FIG.; 11) or a cap CP (FIG. 8) of elastomeric material that allows the hydraulic seal also after the perforation of a sharpened member (defluxion device).

According to another embodiment of the invention according to the FIGS. 9 and 10, the closing wall (c) is replaced or completed with a removable element (e) that can (or cannot) be integral with the same body (c); said element (e) being possibly provided with elements (e.g. ring, tang and similar ones) for making easier its removal.

Another embodiment of the invention is represented in the FIG. 7, and is characterized in that the body 1 is supplied laterally with a second chamber (f) suitable for holding the elastic memory element 2. The hydraulic seal of this element 2 is carried out as previously described, further the body (f) shows a wall (g) that can be penetrated easily with needles, syringes, etc.

According to a further development of the system according to the FIG. 7, the wall g is located on the upper wall, closing in this way the elastic element 2 into a sterile or sterilizing room.

Further the valve body described in the FIG. 11 shows the advantage of an easy positioning with respect to the flexible container, considering the guide surface generated between the lateral external surfaces of the second chamber (f) and the same body. This zone can have a cylindrical, conical, pyramidal, prismatic, spheric or elliptic shape or any combination of the said curves in the space.

As the FIG. 1 shows, the part protruding towards the outside (b) can have a continuous crown AL having inner diameter inferior to the one of the cylindrical part (b), that is used for guide and seal on the defluxion device, when this one is introduced. The continuous crown can be replaced with two or more fins AL distributed on the circumference of (b).

FIG. 12 shows a system in which the elastomeric element 2 contained in the chamber f closed by top wall g is, as in FIG. 11, lateral to a valve body formed of aligned walls (a) and b (as in FIG. 4). The wall portion (b) has a continuation (b') on which is engaged the cylindrical element 14 carrying defluxor 4 held by the open crown AL. Normally the defluxor-carrier element 14 is pre-inserted on V, i.e. V is provided of 14 at the moment of its fabrication, thus before its use. To insert defluxor 4 (more precisely, its lower cornered portion 44) inside the liquid (SP) containing body CC, it is possible to push downwardly (as in FIG. 11) the same defluxor 4 which goes thus in its dashed position 4' whereby the liquid extracting portion 44' enters the body CC. In this case a relative axially downward movement of the defluxor 4 over body 14 (held stationary) takes place. Fins on crown AL are sufficiently elastic to hold 4 but allows the defluxor 4 to slide downwardly when it is pushed. In many cases it is preferred to make crown AL sufficiently rigid, the defluxor 4 does not slide over cylinder 14 but the lower portion 14' of defluxor-carrier 14 is internally threaded and engages the corresponding outer thread F of the portion (b) of valve V. In rest conditions defluxor-carrier 14 and portion (b) are screwed as in FIG. 12, i.e. 14 is engaged with the threaded portion F or equivalently by forcing it under pressure (absence of F). In operative conditions i.e. when defluxor has to perforate and penetrate CC (4 takes position 4'), thread 14' is tightly screwed on the portion F' of external thread F, F' having such a length to bring end 15 of 14 in position 15', 4 in 4' and 44 in 44' (inside CC). With this second solution (4 integral with 14) defluxor 4 is connected to valvular body V of bag BS from the very beginning when it is not in communication with liquid SP contained in BS; this pre-insertion can be carried out either by screwing thread F or simply by forcing 4 under pressure in 14; to bring defluxor 4 in contact with the inside of bag (and thus with the peritoneus in the case of CAPD dyalisis according to Assignee's U.S. Pat. No. 4,306,976) it is sufficient to rotate 14 till the bottom of F' whereby it goes in its work condition 44'.

In a preferred embodiment, both elements V and 14 are stationary and engaged only on thread F, and defluxor 4 carries out a rotation around its longitudinal axis and then it descends towards CC to perforate it.

According to FIGS. 12, 13 (schematic fragmentary view similar to that of FIGS. 12) and 14 (schematic fragmentary top view of FIG. 13), the defluxor-carrier 14 comprises a second inner cylindrical portion showing on its top circumference two couples of shoulders 19—19' and 21—21' and two slots 18-18', each shoulder or slot of a couple being diametrically opposed to the other shoulder respectively slot. On the other side defluxor 4 is provided with two transversal projections 20—20' having quadrangular or rectangular cross-section.

In a first stage defluxor 4 is inserted in 14 with its projections 20—20' on shoulders 21—21' assuming thus a rest position in which 4 (and thus 44) are not in contact with bag CC. When in a second stage, defluxor 4 is to be used to perforate bag wall CC and get in contact with the therein contained liquid SP to bring it through tube T to a patient, it is firstly rotated clockwise to bring projections 20—20' in alignment with slots 18—18' and then pushed down to the bottoms 22—22' thereof. The longitudinal extension of 18—18' is such that defluxor 4 goes in position 4' and its perforator 44 in 44' when projections 20—20' are pushed down from upper seats 21—21' (rest position) to the working positions on said bottoms 22—22' of slots 18—18' having an opening slightly larger than the cross-section of projections 20—20' which can thus slide therein. The upper shoulders 19—19' serve as seats to an upper ring (not shown) which closes and thus protects the upper face of the element 14 and thus the defluxor 4.

With the defluxor, pre-insertion advantages are obtained in the handling of perfusional solutions, particularly when two solution contained in two different bags are to be given at the same time to a patient and are mixed only at the very last moment of delivery because the preparation of the mixture in only one bag is ------------------------------------ incompatible (e.g. a sugar concentrated solution and an amino acid solution, or a bicarbonate solution and a Ca ion solution). In this case the two bags containing the two incompatible liquids are prepared separately, then are each provided with valves having pre-insertion defluxors, the two valves are connected to one tube before sterilization and finally the whole system is sterilized.

Only at the very moment of the use, the cylinder bodies of the valves are completely screwed, the defluxors penetrate the bag bodies CC and the two solutions are mixed "in closed circuit" without any risk of external contamination.

We claim:

1. A valvular system for the extraction and/or addition of liquids held in a flexible sterilizable container of plastic material, comprising:

a housing body, formed of a single piece of flexible plastic film material different from that of the container, having a first wall adjacent to and sealed to said container, and a second wall parallel to said first wall and remote from said container; and an elastomeric element contained within said housing body forming a hydraulic seal with said housing body, said elastomeric element having a plurality of faces, wherein the face of said elastomeric element remote from said container is spaced from the second wall of said housing body, thereby creating sterilizable chamber within said housing body, said sterilizable chamber having a width smaller than the width of said elastomeric element.

2. A valvular system as recited in claim 1, wherein said second wall of said housing body includes an indentation in the shape of an upset cone for facilitating the penetration of a sharpened member which allows the extraction and/or addition of liquid into said container.

3. A valvular system as recited in claim 1, wherein said housing body includes a protuberance comprising an inner crown of preferably elastic material directed towards the center of said sterilizable chamber, said inner crown applying a proper pressure to form a hydraulic seal against the surface of a defluxor.

4. A valvular system as recited in claim 1, further comprising a second elastomeric element for the introduction of liquid into said flexible sterilizable container, said second housing being displaced longitudinally from said first housing.

5. A valvular system as recited in claim 4, wherein a defluxor is preinserted in a cylindrical carrier, said cylindrical carrier being slidable from a first position to a second position over said first housing such that said defluxor perforates said flexible sterilizable container in said second position.

6. A valvular system as recited in claim 4, wherein a defluxor is preinserted in a cylindrical carrier, said cylindrical carrier being attachable to said first housing by a rotation action, first rotation action causing a preinsertion of said defluxor onto said first housing body, and a further rotation causing said defluxor to perforate said flexible sterilizable container.

7. A valvular system as recited in claim 4, further comprising a defluxor having two projections, a cylindrical carrier for said defluxor having on its circumference a first pair of upper shoulders which act as a seat for a closing ring, a second pair of lower shoulders which act as a seat for said projections when said defluxor is in a first rest position, and a pair of longitudinal slots having an opening slightly larger than the cross section of said projections and a longitudinal extension, whereby by first rotating said defluxor around its longitudinal axis to bring said projections in alignment with said longitudinal slots, and then by pushing said projections down said slots, said defluxor is moved from its first position to a position in which it perforates said flexible sterilizable container.

* * * * *